(12) United States Patent
Fecher et al.

(10) Patent No.: US 8,444,914 B2
(45) Date of Patent: May 21, 2013

(54) PROCESS FOR THE POLISHING OF METALLIC DENTAL PROSTHESES

(75) Inventors: Stefan Fecher, Johannesberg (DE); Martin Haizmann, Glauburg (DE); Lothar Volkl, Goldbach (DE); Lars Weisensel, Johannesberg (DE)

(73) Assignee: Degudent, Hanau (DE)

( * ) Notice: Subject to any disclaimer, the term of this patent is extended or adjusted under 35 U.S.C. 154(b) by 1464 days.

(21) Appl. No.: 12/050,307

(22) Filed: Mar. 18, 2008

(65) Prior Publication Data

US 2008/0230397 A1 Sep. 25, 2008

(30) Foreign Application Priority Data

Mar. 19, 2007 (DE) .......................... 10 2007 013 638

(51) Int. Cl.
*C22C 32/00* (2006.01)
(52) U.S. Cl.
USPC .............................. 419/26; 205/674; 205/640
(58) Field of Classification Search
USPC .......................................................... 419/26
See application file for complete search history.

(56) References Cited

U.S. PATENT DOCUMENTS

| 4,606,887 | A | | 8/1986 | Hausselt et al. |
| 5,028,304 | A | * | 7/1991 | Stanishevsky et al. ....... 205/674 |
| 2005/0186538 | A1 | | 8/2005 | Uckelmann |
| 2005/0232806 | A1 | | 10/2005 | Lindigkeit |
| 2006/0180637 | A1 | | 8/2006 | Strietzel |

FOREIGN PATENT DOCUMENTS

| DE | 225873 | 9/1910 |
| DE | 682248 | 10/1939 |
| DE | 944692 | 6/1956 |
| DE | 3210315 | 9/1983 |
| DE | 238074 | 8/1986 |
| DE | 19815091 | 10/1998 |
| DE | 10136997 | 2/2003 |
| DE | 10207632 | 9/2003 |
| WO | WO 2006/079188 A1 * | 8/2006 |

OTHER PUBLICATIONS

John J Dunkley, "Atomization," ASM Handbook, vol. 7, 1998, pp. 35-52.*

* cited by examiner

*Primary Examiner* — Roy King
*Assistant Examiner* — Christopher Kessler
(74) *Attorney, Agent, or Firm* — Ladas & Parry LLP

(57) ABSTRACT

The invention concerns a process for the polishing of metallic dental prostheses, such as frames. In order to reproducibly obtain a defined surface roughness with no need for additional finishing, it is proposed for the dental prosthesis to be polished by means of plasma polishing.

16 Claims, No Drawings

PROCESS FOR THE POLISHING OF METALLIC DENTAL PROSTHESES

The invention concerns a process for the polishing of metallic dental prostheses, such as frames. The invention also concerns a process for the manufacture of a metallic dental prosthesis.

DE-A-101 36 997 discloses a cobalt dental alloy with at least one precious metal, which is suitable for the manufacture of dental prostheses. These are manufactured by casting the dental alloy. In order to increase the fine granularity of the alloy, accompanying metals such as gallium, germanium, indium, tin and/or aluminum can be added. This lowers the degree of brittleness and increases resistance to corrosion. Appropriate prostheses can be covered with plastic or with ceramic.

In order to smooth the surface after casting, mechanical polishing processes are customarily applied.

DE-B-944 692 refers to an anode bath for metal polishing, which contains an alkali citrate or ammonium citrate and water, whereby the pH value is between 4 and 7.

DE-B-225 873 discloses a process for the electrolytic treatment of metallic surfaces, in which a voltage of no more than a maximum of 2 to 3 V is applied between the electrodes which are placed in the electrolyte.

A mixture of sulfuric acid, water and glycerin is used as the electrolyte, in order to give stainless iron and steel alloys a shiny appearance (DE-B-682248).

The object of DD-A-238 074 is a process for providing a high-gloss finish to current-conducting workpieces in the anodic electrolyte plasma. The workpieces in question consist of multi-phased alloys.

An electrolytic polishing treatment of cobalt-chromium or titanium alloys is known from DE-C-32 10 315.

The plasma polishing of titanium and titanium alloys is described in DE-A-102 07 632. The electrolyte solution used has a pH value of between 5.0 and 7.0.

EP-A-1 568 472 discloses a process for free-form sintering and/or melting which is used for the manufacture of dental products. In this process, a laser or electron beam is projected in such a way, that positions on the material layer to be formed are irradiated numerous times, in order to reduce total manufacturing times.

DE-C-33 19 457 refers to a cobalt-chromium alloy which is suitable for use as a thermal casting alloy for a fixed or removable dental prosthesis.

An additional cobalt-chromium alloy is described in EP-A-1 696 044. This alloy does not contain aluminum, but does contain gallium in a range between 2% and 4% by weight.

A dental casting alloy according to WO-A-2004/042098 contains 25% to 32% by weight of chromium, 8% to 12% by weight of tungsten, 0.05% to 0.4% each by weight of one or more of the elements in Groups 4 and 5 of the periodic table, impurities as a result of manufacturing, and cobalt as the remainder.

The object of DE-A-198 15 091 is an ally for cast dental parts consisting of 20% to 35% by weight of chromium, 4% to 8% by weight of molybdenum, up to 3% by weight of silicon, between 0.05% and 1.2% by weight of tantalum, niobium and/or tungsten, whereby the proportion of each of the last three elements is less than 0.5% by weight, up to 0.3% by weight of carbon, 0.05% to 0.4% by weight of nitrogen, up to 3% by weight of iron, up to 3% by weight of manganese, less than 1% by weight of possible impurities, and cobalt as the remainder.

The present invention is based on the task of providing a process for the polishing of metallic dental prostheses of the type set forth in the opening passage of this document, in such a way, that a defined degree of surface roughness can be reproducibly achieved, with no necessity for additional finishing, as is customarily required in mechanical polishing processes. The invention further refers to a process for the manufacture of a metallic dental prosthesis made of a cobalt-chromium alloy which exhibits good processing behavior. To this end, the tendency to fracture should be minimized, whereby hardness values which enable problem-free additional finishing should be achieved. In addition, corrosion rates in the range of precious metals should be achieved.

One aspect of this task is solved according to the invention by having the dental prosthesis, which is made of a cobalt-chrome alloy with a composition of 50% to 65% by weight of cobalt, 15% to 22% by weight of chromium, 15% to 22% by weight of tungsten, 4% to 11% by weight of iron, 1% to 3% by weight of aluminum and 0% to 10% by weight of molybdenum, be polished by plasma polishing, whereby the dental prosthesis during the plasma polishing process is immersed in an electrolyte in the form of a mixture of water and at least one ammonium salt and the electrolyte has a pH value of $1 \leq pH \leq 3$.

According to the invention, a dental alloy is smoothed by plasma polishing, in order to obtain a defined surface, which, in cases where a facing (covering) process is to take place, is intentionally roughened, for example, by sandblasting. If a facing (covering) process is not to take place, the resultant surface is quite smooth, leading to increased resistance to corrosion.

Optimum results are obtained when the plasma polishing is performed at a current density of 0.25 A/cm$^2$ to 0.5 A/cm$^2$. The voltage should be between 300V and 380V, whereby the dental prosthesis serves as the anode in the plasma polishing.

In order to optimize the process, the invention provides for the electrolyte, at the beginning of the plasma polishing, to be at a temperature T, where $T_s-2°$ C.$\geq$T, whereby $T_s$=the boiling temperature of the electrolyte. The electrolyte should in particular be at a temperature of 80° C.$\leq$T$\leq T_s-2°$ C.

The plasma polishing should take place, in particular, over a period of time of up to 15 minutes, preferably less than 10 minutes.

The polishing process according to the invention, especially in the case of dental prostheses which are manufactured by laser sintering and/or laser melting, guarantees that the surface unevenness produced by manufacturing is reduced in such a way that the resultant surface layer is amorphous and grasslike, with a low specific surface. This increases the resistance to corrosion, due to the low proportion of ions released into the environment, in comparison to mechanically polished surfaces.

It is especially provided for the cobalt-chrome alloy to additionally contain 0% to 0.2% by weight of at least one of the elements boron and yttrium, 0% to 2% by weight of at least one of the elements vanadium, silicon, copper, zinc, niobium, 0% to 10% by weight of gallium, 0% to 5% by weight of germanium and 0% to 1% by weight of at least one of the elements cerium and lanthanum. Moreover, the alloy should not contain more than 50% by weight of chromium, tungsten and rhenium. In addition, the invention is characterized by the fact that the proportion of chromium:tungsten+rhenium is between approximately 2:3 and approximately 2:1, or between approximately 2:3 and approximately 3:2.

One embodiment of the invention provides for the content of chromium+tungsten to be at least 30% by weight and at most 50% by weight, and for the proportion of chromium:tungsten to be between approximately 3:4 and approximately 4:3.

According to an especially preferred embodiment, the process according to the invention is not for metallic dental prostheses which are manufactured by casting, but rather by laser sintering and/or laser melting processes—that is, in principle, according to a process such as that described in DE-C-196 49 865, to the publication whereof we hereby refer.

In other words, the process used is a rapid prototyping process, in which the alloy powder is applied in one layer after another, and each layer of powder, prior to the application of the next layer, is heated by means of a focused laser beam in a predefined area, which corresponds to a selected cross-section area of the dental prosthesis, to a predefined temperature, in such a way that the layer of powder is attached to the layer below it by the melting and/or sintering of the powder layer.

Accordingly, the invention is also characterized by a process for the manufacture of a metallic dental prosthesis, such as a frame, through the use of a cobalt-chromium alloy with a composition of

- 43% to 68% by weight of cobalt,
- 12% to 30% by weight of chromium,
- 8% to 25% by weight of tungsten,
- 0% to 13% by weight of iron,
- 0% to 30% by weight of manganese,
- 0% to 10% by weight of molybdenum,
- 0% to 5% by weight of at least one of the elements aluminum, tantalum, rhenium, titanium, and less than 0.1% by weight of carbon, whereby the cobalt-chromium alloy is sprayed in powder form and the dental prosthesis is manufactured by means of a rapid prototyping process and subsequently polished by plasma polishing.

Surprisingly, the cobalt-chromium alloy of the composition set forth above enabled the manufacture of a dental prosthesis by laser melting and/or laser sintering, whereby the aforesaid dental prosthesis exhibits breaking elongation characteristics similar to those known from casting alloys. Just as surprisingly, however, the resulting corrosion rate is less than 10 μg/cm$^2$ in 7 days, measured according to DIN 22674, which lies by more than a factor of 6 below the corrosion value of a dental casting alloy of the same composition.

The corrosion rate according to DIN 22674 is determined by placing a small plate of the alloy—manufactured by casting, or by laser melting and/or laser sintering—in a test solution which corresponds to ISO 10271, in order then to determine the quantity of materials dissolved out of the plate after 7 days, when the surface area of the plate is known.

In addition to the outstanding resistance to corrosion, the good mechanical properties obtained are also surprising. Both of these phenomena may possibly be explained by the fact that the kinetics of the intermetallic phases are affected by the laser melting or laser sintering, so that the phases, in contrast to casting, cannot be formed in such a way as to give rise to the known negative properties of cast alloys.

In addition, the dental prosthesis obtained, prior to additional heat treatment, has a hardness of less than 350 (HV 10), so that good additional finishing is possible. However, in cases where heat treatment is necessary, in order to eliminate distortions, measurements have shown that the hardness increases to over 400 (HV 10); nevertheless, however, good additional finishing is possible—a property which was not foreseeable.

The properties of the dental prosthesis and/or frame are especially positive when the manufacturing process is accomplished by laser melting, so that the individual layers of powder are completely melted one after the other. On each melted and subsequently solidified layer, an additional layer of powder is applied, which in turn is completely melted and thereby surface-fused to the layer below it. These procedural steps are performed in succession, in order to achieve the desired geometry of the dental prosthesis or frame being manufactured, by means of free-form melting.

It is especially possible for the alloy to contain 50% to 65% by weight of cobalt, 15% to 22% by weight of chromium, 15% to 22% by weight of tungsten, 4% to 11% by weight of iron and 1% to 3% by weight of aluminum.

The cobalt-chrome alloy can contain tungsten and/or molybdenum, with a content between 8% and 35% by weight each.

It is additionally possible for the cobalt-chrome alloy to contain 0% to 0.2% by weight of at least one of the elements boron and yttrium, 0% to 2% by weight of at least one of the elements vanadium, silicon, copper, zinc, niobium, 0% to 10% by weight of gallium, 0% to 5% by weight of germanium and 0% to 1% by weight of at least one of the elements cerium and lanthanum.

In any event, the alloy should not contain more than 50% by weight of chromium, tungsten and rhenium.

Preferably, the proportion of chromium:tungsten+rhenium is between approximately 2:3 and approximately 2:1, or between approximately 2:3 and approximately 3:2.

The content of chromium+tungsten is at least 30% by weight and at most 50% by weight, and the proportion of chromium:tungsten is between approximately 3:4 and approximately 4:3.

With regard to the composition of the electrolyte and its pH value regulation, or the parameters which should preferably be maintained in plasma polishing, reference is hereby made to the embodiments set forth above.

The invention claimed is:

1. Process for the manufacture of a metallic dental prosthesis through the use of a cobalt-chromium alloy with a composition of:
   - 43% to 68% by weight of cobalt,
   - 12% to 30% by weight of chromium,
   - 8% to 25% by weight of tungsten,
   - 0% to 13% by weight of iron,
   - 0% to 30% by weight of manganese,
   - 0% to 10% by weight of molybdenum,
   - 0% to 5% by weight of at least one of the elements aluminum, tantalum, rhenium, titanium,
   - and less than 0.1% by weight of carbon, whereby the cobalt-chromium alloy is sprayed in powder form and the dental prosthesis is manufactured by means of a rapid prototyping process and subsequently polished by plasma polishing; and
   immersing the dental prosthesis in an electrolyte in the form of a mixture of water and at least one ammonium salt during the plasma polishing, wherein the electrolyte has a pH value of $1 \leq pH \leq 3$.

2. Process according to claim 1, characterized in that the alloy contains 50% to 65% by weight of cobalt, 15% to 22% by weight of chromium, 15% to 22% by weight of tungsten, 4% to 11% by weight of iron and 1% to 3% by weight of aluminum.

3. Process according to claim 1, characterized in that ammonium sulfate or ammonium hydrogen sulfate is used as the ammonium salt.

4. Process according to claim 1, characterized in that sulfuric acid is added to the electrolyte in order to set the pH value.

5. Process according to claim 1, characterized in that the plasma polishing is performed at a current density of 0.25 A/cm$^2$ to 0.5 A/cm$^2$.

6. Process according to claim 1, characterized in that the plasma polishing is accomplished at a voltage U of 300V<U<380V applied between the dental prosthesis as anode and a cathode.

7. Process according to claim 1, characterized in that the electrolyte, at the beginning of the plasma polishing, is at a temperature T, where $T_s - 2°\text{C} \geq T$, whereby $T_s$=a boiling temperature of the electrolyte.

8. Process according to claim 1, characterized in that the electrolyte, at the beginning of the plasma polishing, is at a temperature T, where $80°\text{C} \leq T \leq T_s - 2°\text{C}$, whereby $T_s$=a boiling temperature of the electrolyte.

9. Process according to claim 1, characterized in that the dental prosthesis is plasma-polished over a time t where $t \leq 15$ min.

10. Process according to claim 1, characterized in that the metallic dental prosthesis which is plasma-polished is one which was manufactured by means of a laser sintering and/or laser melting process.

11. Process according to claim 1, characterized in that the cobalt-chrome alloy additionally contains 0% to 0.2% by weight of at least one of the elements boron and yttrium, 0% to 2% by weight of at least one of the elements vanadium, silicon, copper, zinc, niobium, 0% to 10% by weight of gallium, 0% to 5% by weight of germanium and 0% to 1% by weight of at least one of the elements cerium and lanthanum.

12. Process according to claim 1, characterized in that the alloy does not contain more than 50% by weight of chromium, tungsten and rhenium.

13. Process according to claim 1, characterized in that the proportion of chromium:tungsten+rhenium is between approximately 2:3 and approximately 2:1.

14. Process according to claim 1, characterized in that the content of chromium+tungsten is at least 30% by weight and at most 50% by weight, and the proportion of chromium:tungsten is between approximately 3:4 and approximately 4:3.

15. Process according to claim 1, characterized in that the dental prosthesis is plasma-polished over a time t where $t \leq 10$ min.

16. Process according to claim 1, characterized in that the proportion of chromium:tungsten+rhenium is between approximately 2:3 and approximately 3:2.

* * * * *